US011205335B2

(12) United States Patent
Dongre (10) Patent No.: US 11,205,335 B2
(45) Date of Patent: Dec. 21, 2021

(54) LANYARD DEVICE, METHOD AND PERSONAL LANYARD MONITORING SYSTEM

(71) Applicant: Lifeline Systems Company, Framingham, MA (US)

(72) Inventor: Chaitanya Dongre, Vaals (NL)

(73) Assignee: Lifeline Systems Company, Framingham, MA (US)

( * ) Notice: Subject to any disclaimer, the term of this patent is extended or adjusted under 35 U.S.C. 154(b) by 699 days.

(21) Appl. No.: 15/999,442

(22) PCT Filed: Feb. 8, 2017

(86) PCT No.: PCT/EP2017/052666
§ 371 (c)(1),
(2) Date: Aug. 15, 2018

(87) PCT Pub. No.: WO2017/140537
PCT Pub. Date: Aug. 24, 2017

(65) Prior Publication Data
US 2021/0209920 A1 Jul. 8, 2021

(30) Foreign Application Priority Data

Feb. 16, 2016 (EP) ..................................... 16155907

(51) Int. Cl.
*G08B 23/00* (2006.01)
*G08B 21/04* (2006.01)
(Continued)

(52) U.S. Cl.
CPC .......... *G08B 21/043* (2013.01); *A61B 5/1117* (2013.01); *A61B 5/1118* (2013.01);
(Continued)

(58) Field of Classification Search
CPC .. G08B 21/043; G08B 21/0446; A61B 5/746; A61B 5/1117; A61B 5/1118;
(Continued)

(56) References Cited

U.S. PATENT DOCUMENTS 8,145,386 B2    3/2012 Harase
9,984,548 B2 *  5/2018 Kechichian ............ G08B 21/02
(Continued)

FOREIGN PATENT DOCUMENTS

EP    2087835 A1    8/2009
EP    2549228 A1    1/2013
(Continued)

OTHER PUBLICATIONS

Tao et al: "Gait Analysis Using Wearable Sensors"; Sensors 2012, vol. 12, pp. 2255-2283.
(Continued)

*Primary Examiner* — Julie B Lieu
(74) *Attorney, Agent, or Firm* — Honigman LLP; Grant Griffith (57) ABSTRACT

A lanyard device (10) having a flexible neck cord (12) and at least one strain sensor (30) arranged for sensing strain in the flexible neck cord; and a personal lanyard monitoring system including the lanyard device (10). A position recognition unit (52) is configured for comparing strain data obtained from the at least one strain sensor (30) to predetermined strain data, and recognizing a position of the flexible neck cord (12) in dependence on a result of the comparison.

11 Claims, 4 Drawing Sheets

(51) Int. Cl.
*A61B 5/11* (2006.01)
*A61B 5/00* (2006.01)

(52) U.S. Cl.
CPC ............ *A61B 5/6822* (2013.01); *A61B 5/746* (2013.01); *G08B 21/0446* (2013.01); *A61B 2560/0214* (2013.01); *A61B 2562/0266* (2013.01)

(58) Field of Classification Search
CPC .......... A61B 5/6822; A61B 2562/0266; A61B 2560/0214; A61B 6/1117; A61B 6/1118; A61B 6/6822; A61B 6/746
See application file for complete search history.

(56) References Cited

U.S. PATENT DOCUMENTS

| | | | | |
|---|---|---|---|---|
| 2008/0234898 | A1* | 9/2008 | Wiener | G01G 3/125 701/45 |
| 2009/0185772 | A1* | 7/2009 | Xia | G01K 11/3206 385/13 |
| 2010/0245078 | A1* | 9/2010 | Nadkarni | G08B 21/043 340/539.11 |
| 2012/0324946 | A1 | 12/2012 | Latouf | |
| 2014/0077946 | A1 | 3/2014 | Tran | |
| 2014/0114142 | A1 | 4/2014 | Shaoulian | |
| 2015/0123785 | A1* | 5/2015 | Haflinger | A61B 5/6822 340/539.11 |
| 2015/0226764 | A1* | 8/2015 | Ten Kate | G01P 15/00 702/141 |
| 2016/0073886 | A1* | 3/2016 | Connor | A61B 5/6887 600/475 |
| 2016/0275771 | A1* | 9/2016 | Visweswara | A61B 5/1117 |
| 2017/0191835 | A1 | 7/2017 | Ou et al. | |

FOREIGN PATENT DOCUMENTS

| | | |
|---|---|---|
| GB | 2492754 A | 1/2013 |
| JP | 2015011631 A | 1/2015 |
| WO | 2009112281 A1 | 9/2009 |
| WO | 2011004322 A1 | 1/2011 |
| WO | 2015055439 A1 | 4/2015 |
| WO | 2015055439 A1 | 7/2015 |

OTHER PUBLICATIONS

Office Action, Application No. 201847031114, dated Jun. 24, 2021, 7 pages.

* cited by examiner

LANYARD DEVICE, METHOD AND PERSONAL LANYARD MONITORING SYSTEM

CROSS-REFERENCE TO PRIOR APPLICATIONS

This application is the U.S. National Phase application under 35 U.S.C. § 371 of International Application No. 2017/EP2017/052666, filed on Feb. 8, 2017, which claims the benefit of European Patent Application No. 16155907.5 filed on Feb. 16, 2016. These applications are hereby incorporated by reference in their entirety herein.

FIELD OF THE INVENTION

The invention relates to the field of lanyard devices of e.g. personal emergency response systems.

BACKGROUND OF THE INVENTION

Tao, W. et al., Gait Analysis Using Wearable Sensors, Sensors (Basel, Switzerland), ISSN 1424-8220, 2012, 12(2): 2255-2283, doi:10.3390/s120202255, mentions the usage of flexible goniometers to measure the relative rotation between two human body segments in gait analysis, including strain gauges, mechanical, flexible, inductive, and optical fiber goniometers.

WO 2009/112281 A1 relates to an upper body garment, comprising an apparatus for detection of the orientation of at least one body segment integrated to the garment.

EP 2087835 A1 relates to a fall detector comprising a necklace with a total length laying in a range of thirty up to eighty centimeters.

US 2014/0077946 A1 relates to a personal emergency response system that includes one or more sensors to detect activities of a mobile object.

US 2014/0114142 A1 relates to a patient monitor system including a pendant configured to be worn around a neck of a patient.

SUMMARY OF THE INVENTION

It has been found that in the U.S.A., falls are a major cause of injury among the elderly population.

It would be advantageous to achieve a device and system that allows for an improved fall detection and/or fall prevention. In particular, with regard to a personal emergency response system, it would be desirable to improve detection of a fall of a person, or detection of a period of non-activity.

It would also be advantageous to achieve a device and system that may contribute to improving wear compliance of a lanyard device, e.g. a personal health device, or a lanyard device of a personal emergency response system. Naturally, wearing compliance is an important factor in a personal emergency response system.

With regard to a personal device for monitoring sport activities, it would be desirable to be able to automatically recognize an activity of a person, e.g. lying, sitting, standing, walking, running, going by bike. In particular, it would be desirable to be able to automatically recognize a position or posture during (non-)activity for better estimation or calculation of further parameters, such as calorie expenditure.

To better address one or more of these concerns, in a first aspect of the invention, a lanyard device is presented that comprises:

a flexible neck cord; and at least one strain sensor arranged for sensing strain in the flexible neck cord.

A lanyard device with a flexible neck cord has the advantage that it may be configured to be comfortable to wear. In particular, and in contrast to a strain sensor integrated in specific clothes, a lanyard device may be provided independent of any clothes. Thus, it is made possible to provide for a very lightweight device.

When the lanyard device is worn around the neck by a person, it may assume a position that is determined by the shape of the neck and by the posture of the person. In particular, the position will be different depending on whether the person is lying or standing. On the other hand, when the lanyard device is not being worn, the position may be still different. For example, the lanyard device may be used with a personal activity tracker or a personal emergency response system.

When the lanyard device is worn around the neck of a person, gravitational forces due to the weight of the lanyard device and/or a pendant arranged on the lanyard device may exert a stress on the neck cord, causing strain of the flexible neck cord. Moreover, when the flexible neck cord may assume a position under the influence of gravity acting on the lanyard device, this may be beneficial for detecting strain and relating a detected strain to a position or an activity. For example, strain is sensed in at least one portion of the flexible cord.

For example, the sensed strain may comprise strain induced by gravity pulling on a pendant attached to the flexible neck cord.

For example, sensing the strain may allow for distinguishing between a period in which sensed strain varies, which may be associated with activity, and a period of constant sensed strain, which may be associated with non-activity, sedentary activity, or non-wearing of the lanyard device. For example, sensing the strain in the neck cord may allow for detecting activity of a person wearing the lanyard device. For example, an activity like walking may result in a variation of strain in the neck cord. On the other hand, when the lanyard device is lying motionless, the sensed strain will be constant. For example, when the lanyard device is lying on a flat surface, e.g. a table, the sensed strain will be about zero; that is, there will be no strain.

In particular, sensing strain in the flexible neck cord may allow for distinguishing a non-wearing state of the lanyard device from a state associated with activity of a person wearing the lanyard device. Thus, for example, a system including the lanyard device may be configured for detecting a non-wearing state of the lanyard device. Thus, by outputting an alert signal or alert message, a person may be reminded to put on the lanyard device. Furthermore, a personal emergency response system center may be alerted.

In particular, the lanyard device may be configured for forming a closed loop to be worn around the neck of a person. For example, the lanyard device forms a closed loop. For example, the closed loop includes the flexible neck cord or is formed by the flexible neck cord.

In some embodiments, the flexible neck cord comprises at least two sensing elements of the at least one strain sensor, the at least two sensing elements being arranged one after another at different positions along the flexible neck cord, wherein the at least one strain sensor is configured for outputting separate strain data respectively corresponding to sensed strain of the at least two respective sensing elements. Thus, strain may be sensed at different positions distributed along the flexible neck cord. Thus, sensor readings of the at least two sensing elements are provided by the at least one strain sensor. The separate strain data may be combined to a strain distribution or may be output by the sensor in form of a strain distribution along the flexible neck cord. Thus, a spatial distribution of strain over the at least two sensing elements, or strain sensitive sections, of the flexible neck cord may be provided. For example, different postures or positions may result in distinguishable elongation patterns, and, thus, strain patterns, of the neck cord. Multiple sensing elements may provide for a good representation of the strain distribution along the neck cord, or may allow for at least monitoring important segments of the neck cord.

In some embodiments, the at least one strain sensor comprises at least one fiber optic strain sensor, which, in the following, may also be called an optical fiber strain sensor.

An optical fiber strain sensor is advantageous in that it may be configured to be very lightweight, waterproof, and have a very low power requirement. A lightweight lanyard device is advantageous in that it may be comfortably worn. This is may e.g. improve wearing compliance in case of a personal emergency response system. Waterproof configuration is advantageous in that it allows for wearing the lanyard device even in the bath room, where falls are common. A low power requirement may have the advantage that e.g. a battery powered lanyard device may provide for a long lasting usability, before a battery would have to be replaced. A lightweight and/or water proof configuration is also particularly advantageous for wearing during sports.

For example, the fiber optic strain sensor may comprise at least one optical fiber, a light source for emitting light into the at least one optical fiber, and a light detector for detecting light output from the at least one optical fiber. Infrared (IR) light may be advantageously used. For example, the light source may comprise at least one light emitting diode (LED). The light source may be arranged in the flexible neck cord or in a pendant attached to the flexible neck cord.

For example, at least one optical fiber section that forms a sensing element, i.e. a strain sensitive element, of the at least one fiber optic strain sensor may be arranged in the flexible neck cord. Thus, an optical fiber may form or comprise at least one sensing element of the respective strain sensor.

As a well known kind of optical fiber strain sensor, there may be implemented an optical fiber having a grating, e.g. a Bragg grating, adapted for reflecting a specific light wavelength, wherein the main reflection wavelength is dependent on the grating interval, which changes with the strain experienced by the optical fiber at the position of the grating. Thus, the intensity of the reflected light of a specific wavelength, as well as the intensity of the transmitted light, varies dependent on the strain at the grating. In particular, the magnitude an direction of a shift of the main reflection wavelength is directly proportional to the change in strain.

Thus, the at least one fiber optic strain sensor may comprise at least one fiber Bragg grating based optical sensor.

For example, the at least one fiber optic strain sensor may comprise an optical fiber which comprises at least two strain sensitive sections forming sensing elements of the at least one fiber optic strain sensor, the at least two strain sensitive sections being arranged one after another at different positions along the flexible neck cord, wherein the at least one fiber optic strain sensor is configured for outputting separate strain data respectively corresponding to sensed strain of the at least two respective strain sensitive sections.

Thus, each of the at least one fiber optic strain sensor may comprise an optical fiber having such multiple sections that are strain sensitive, wherein strain of the respective sections may be separately detectable.

Thus, using one optical fiber, strain may be sensed at different positions distributed along the flexible neck cord. For example, the strain sensitive sections may be responsive to different wavelengths of light, at a specific strain. Or, for example, the at least one fiber optic strain sensor may be configured for sensing the time delay of light reflected from a respective strain sensitive section.

In some embodiments, the flexible neck cord includes at least one optical fiber of the at least one fiber optic strain sensor, and a protective cladding arranged around the at least one optical fiber.

For example, the flexible neck cord may include a light protective and/or water protective, i.e. water proof, cladding.

In some embodiments, the lanyard device further comprises a pendant attached to the flexible neck cord. Preferably, the pendant is attached to the flexible neck cord at a fixed position on the flexible neck cord. When the pendant contributes to forming of a position of the flexible neck cord when being worn around the neck of a person, it is advantageous when the pendant has a known position relative to the position of a sensing element of the strain sensor.

In some embodiments, the lanyard device comprises: a pendant attached to the flexible neck cord, the pendant comprising a power source of the at least one strain sensor.

Thus, the weight of the power source may contribute to forming of a position of the flexible neck cord when being worn around the neck of a person.

In some embodiments, the lanyard device comprises: an electronic unit for obtaining strain data from the at least one strain sensor, wherein the electronic unit is configured for at least one of:

processing the strain data;

wirelessly transmitting the strain data; and wirelessly transmitting data derived from the strain data.

For example, the electronic unit may be or comprise a communication unit and/or a position recognition unit.

For example, the electronic unit may be configured for calculating personal activity data dependent on the obtained strain data. For example, time of sports activity may be determined, e.g. time of running, time of walking, and/or estimation of calorie expenditure associated with a period of activity may be calculated dependent on the obtained strain data, e.g. dependent on a time series of recognized positions of the lanyard device.

In some embodiments, the lanyard device comprises:

a communication unit for wirelessly transmitting data derived from the sensed strain.

For example, strain data corresponding to the sensed strain may be transmitted. In particular, for example, separate strain data respectively corresponding to sensed strain of the at least two respective sensing elements or strain sensitive sections may be transmitted. For example, the strain distribution may be transmitted.

For example, the communication unit may be a transmitter. This is sufficient when the lanyard device is not required to comprise a receiver.

For example, the lanyard device may comprise: a portable wireless device coupled to the lanyard device and arranged for obtaining data derived from the sensed strain, the portable wireless device including a transmitter for wirelessly transmitting the obtained data, e.g. strain data.

For example, the portable wireless device may form a pendant attached to the flexible neck cord.

In some embodiments, the lanyard device comprises: a position recognition unit configured for comparing strain data obtained from the at least one strain sensor to pre-determined strain data; and recognizing a position of the flexible neck cord in dependence on a result of the comparison.

Comparing strain data to pre-determined strain data may include comparing magnitude of strain and may include comparing position of strain, the position being taken in a direction along the neck cord.

For example, the obtained strain data and the pre-determined strain data each may comprise a spatial pattern of strain, e.g. a spatial-temporal pattern of strain. A spatial pattern of strain may also be termed a spatial strain distribution.

For example, spatial patterns of sensed strain may allow for distinguishing positions of the lanyard device and, in particular, the neck cord, which positions are associated with predetermined spatial patterns of strain. For example, more positions may be recognizable than based on only a single sensed strain.

For example, more then one position may be recognized, e.g. a series of positions. In particular, a series of positions may be recognized when the obtained strain data includes a temporal pattern of strain, e.g. a spatial-temporal pattern of strain.

For example, a recognized position may be indicative of an activity or inactivity of a person wearing or assumed to be wearing the lanyard device.

Said recognizing a position may be or comprise: determining position data indicative of a position of the flexible neck cord, in dependence on a result of the comparison.

Possible examples of recognized positions of the lanyard device may include:

non-wearing, steady-state, e.g. flat position, associated with non-wearing state of low strain or strain distribution of low strain values, in particular uniform distribution of low strain;

wearing, hanging from neck position, associated with wearing state of characteristic strain or characteristic strain distribution.

Herein, a position associated with non-wearing of the lanyard device is called a non-wearing position.

For example, the pre-determined strain data may include:

pre-determined strain data associated with the lanyard device lying flat; and pre-determined strain data associated with the lanyard device being worn around a neck of a person standing upright.

However, the position recognition unit may be comprised in the lanyard device, or in a communicator remote form the lanyard device.

In a second aspect of the invention, a personal lanyard monitoring system is presented that comprises:

a lanyard device comprising:

a flexible neck cord;

at least one strain sensor arranged for sensing strain in the flexible neck cord; and a communication unit for wirelessly transmitting data derived from the sensed strain, wherein the personal lanyard monitoring system further comprises:

a communicator remote from the lanyard device, wherein the communicator comprises a receiving unit for wirelessly receiving data from the communication unit of the lanyard device.

In some embodiments, at least one of the lanyard device and the communicator comprises: a position recognition unit configured for comparing strain data obtained from the at least one strain sensor to pre-determined strain data; and recognizing a position of the flexible neck cord in dependence on a result of the comparison.

Advantageous features of examples of the position recognition unit have been described above with respect to a position recognition unit of a lanyard device.

Based on a recognized position of the flexible neck cord, or on a variation in time of the recognized position, an activity of a person wearing the neck cord may be deduced. A variation in time of a recognized position may be evaluated in the form of a time sequence of recognized positions.

In some embodiments of the personal lanyard monitoring system, at least one of the lanyard device and the communicator comprises: an activity determining unit configured for determining an activity in dependence on a result of a comparison of strain data obtained from the at least one strain sensor to pre-determined strain data.

Determining an activity may comprise determining inactivity, i.e. absence of activity, such as lying still or sitting/standing.

For example, activities to be determined may include: physical activity such as moving, e.g. walking, or relative inactivity such as standing or sitting.

For example, the activity determining unit may be configured for comparing strain data obtained from the at least one strain sensor to pre-determined strain data.

For example, the activity determining unit may comprise the position recognition unit. For example, the comparison step of the activity determining unit may be performed by the position recognition unit. For example, the activity determining unit may be configured for determining an activity that is associated with a recognized position of the flexible neck or a recognized series of positions of the flexible neck.

For example, the at least one of the lanyard device and the communicator may comprise memory for storing strain data obtained from the at least one strain sensor, and/or for storing recognized positions.

For example, the data derived from the sensed strain that is transmitted by the communication unit of the lanyard device may comprise:

strain data, for example a spatial and/or temporal pattern of sensed strain, position data, for example at least one recognized position recognized by a position recognition unit of the lanyard device, activity data, for example at least one activity determined by an activity determining unit of the lanyard device.

In some embodiments, the strain data and the pre-determined strain data both comprise a at least one respective spatial and/or temporal pattern of strain.

In other words, the respective at least one pattern may be one of: a spatial pattern of strain, a temporal pattern of strain, and a spatial-temporal pattern of strain. The strain data obtained from the at least one strain sensor may comprise: a spatial pattern of sensed strain, a temporal pattern of sensed strain, and a spatial-temporal pattern of sensed strain. The pre-determined strain data may comprise: spatial patterns of strain, temporal patterns of strain, and spatial-temporal patterns of strain.

For example, temporal or spatial-temporal patterns of sensed strain may allow for distinguishing activities associated with predetermined temporal or spatial-temporal patterns of strain. For example, more activities may be recognizable than based on only a single temporal instance of sensed strain or a spatial pattern of sensed strain.

In some embodiments, at least one of the lanyard device and the communicator comprises: a fall detection unit configured for:

detecting a fall of a person presumably wearing the lanyard device in dependence on a result of a comparison of strain data obtained from the at least one strain sensor to pre-determined strain data.

For example, the fall detection unit may be configured for comparing strain data obtained from the at least one strain sensor to pre-determined strain data.

For example, detecting a fall may be based on at least one recognized position of the flexible neck cord or at least one detected activity.

For example, detecting a fall may be performed in dependence on a recognized position or series of positions.

For example, a fall may be assumed when a constant time sequence of recognized positions of a specific duration is detected. The constant time sequence may correspond to a non-activity state of a person presumably wearing the lanyard device. In particular, a fall may be assumed when a sudden change of position of the lanyard device is followed by a non-motion state. This may allow for detecting if a person wearing the lanyard device met with an accident or fell down.

In some embodiments, at least one of the lanyard device and the communicator comprises: a non-wearing determining unit configured for:

determining a non-wearing state of the lanyard device in dependence on a result of a comparison of strain data obtained from the at least one strain sensor to pre-determined strain data associated with non-wearing of the lanyard device.

Thus, monitoring of wearing compliance may be performed.

For example, the non-wearing determining unit may be configured for comparing strain data obtained from the at least one strain sensor to pre-determined strain data associated with non-wearing of the lanyard device.

For example, at least one of the position recognition unit, the activity detection unit, and the fall detection unit may comprise the non-wearing detection unit.

For example, determining a non-wearing state may be performed in dependence on a recognized position or series of positions. For example, the non-wearing determining unit may determine a non-wearing state based on at least one recognized position of the flexible neck cord. That at least one position may be a non-wearing position, for example a position in which the lanyard device is lying flat.

For example, parts of the position recognition unit, the activity determining unit, the fall detection unit, and/or the non-wearing determining unit may be distributed among the lanyard device and the communicator. For example, position recognition may be performed at the lanyard device, whereas determining an activity in dependence on a recognized position or series of positions may be performed at the communicator.

For example, the communicator may comprise an emergency alert unit adapted for transmitting an emergency alert to an emergency response center in case a fall has been detected. Transmitting an emergency alert may comprise performing a telephone call via a telephone line or via mobile communication.

In some embodiments, at least one of the lanyard device and the communicator is configured for initializing at least one personal wearing strain pattern based on strain data obtained from the at least one strain sensor, and storing the at least one personal wearing strain pattern as a part of pre-determined strain data.

Thus, in later comparisons, the personal wearing strain pattern may be compared to current strain data obtained from the at least one strain sensor.

Thus, after initialization, the pre-determined strain data may comprise a personalized wearing pattern based on the shape of the neck of a user and. Since different people might wear the neck cord differently and may have a unique neck circumference or neck shape, initialization of a personal wearing strain pattern allows for improving later detection of a specific strain pattern or position of the neck cord. Thus, recognizing of a position, determining an activity, etc. may be improved.

Thus, for example, a wearing pattern associated with a user wearing the neck cord around the neck in a posture such as a standing position may be initialized.

Initializing may comprise re-initializing or calibrating the personal wearing strain pattern.

In particular, initializing at least one personal wearing strain pattern may comprise: obtaining at least one wearing strain pattern based on sensed strain in a state of the neck cord being worn around the neck of an individual user, and defining at least one personal wearing strain pattern based on the obtained at least one wearing strain pattern. For example, a personal wearing strain pattern may be initialized to an obtained wearing strain pattern, or to an averaged strain pattern of multiple obtained wearing strain patterns.

The initializing may also be implemented in a stand-alone lanyard device.

In a third aspect of the invention, there is provided a method of recognizing a position of a flexible neck cord of a lanyard device, the method comprising:

sensing strain in the flexible neck cord;

obtaining strain data corresponding to the sensed strain;

comparing the obtained strain data to pre-determined strain data; and recognizing a position of the flexible neck cord in dependence on a result of the comparison.

For example, the method may be part of a method of monitoring a lanyard device.

In a fourth aspect of the invention, there is provided a method of monitoring a lanyard device, the method comprising:

sensing strain in the flexible neck cord;

obtaining strain data corresponding to the sensed strain; and comparing the obtained strain data to pre-determined strain data, wherein the method comprises at least one of:

recognizing a position of the flexible neck cord in dependence on a result of the comparison, determining an activity in dependence on a result of the comparison, detecting a fall of a person presumably wearing the lanyard device in dependence on a result of the comparison, and determining a non-wearing state of the lanyard device in dependence on a result of the comparison.

In the above mentioned methods, for example, the steps may be performed recurrently.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
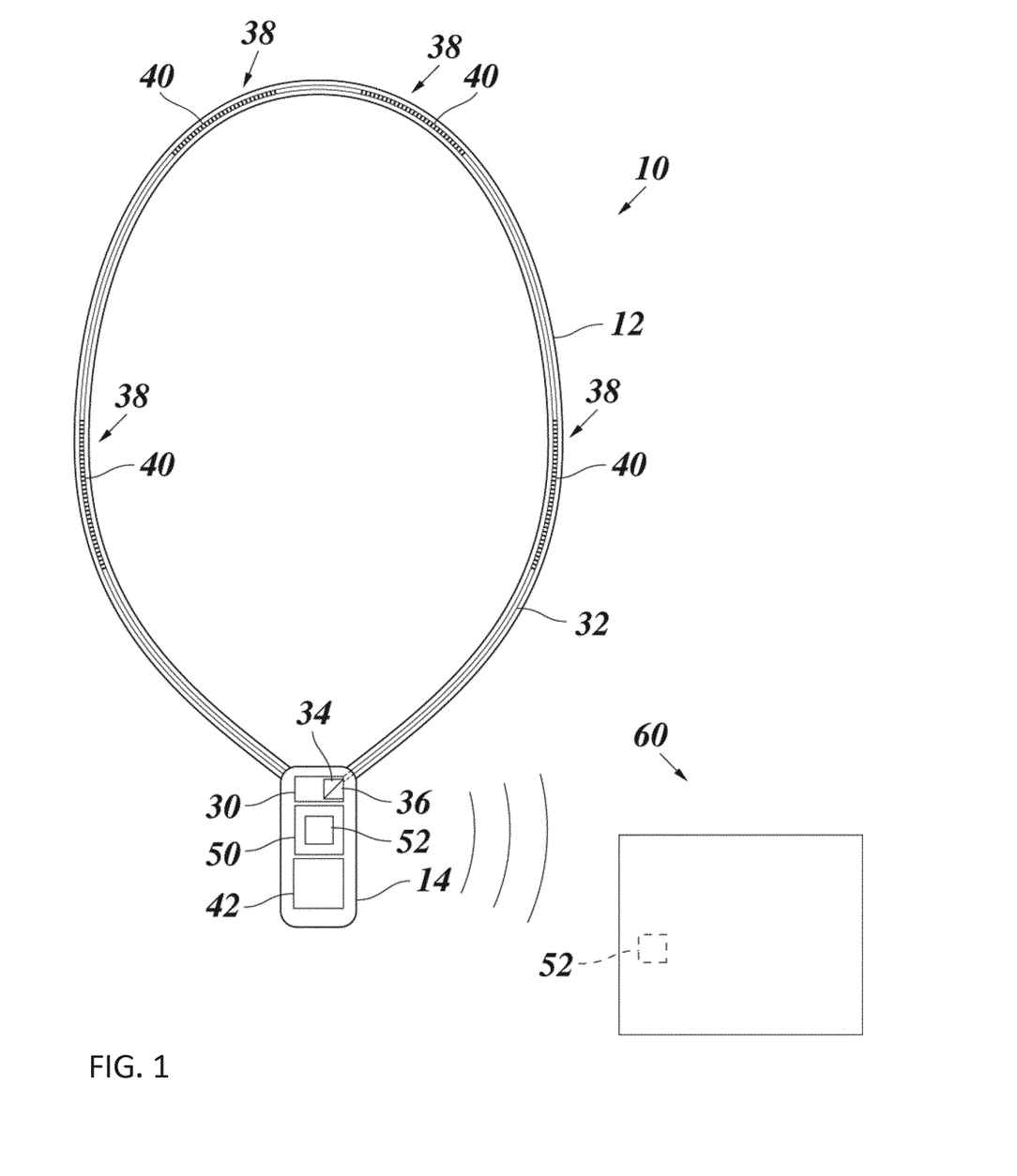
FIG. 1 schematically shows a personal lanyard monitoring system.

FIG. 1 shows a personal lanyard monitoring system having a lanyard device 10 and a communicator 60 remote from the lanyard device 10. The lanyard device 10 is configured to be worn around the neck of a person and has a flexible neck cord 12 that forms a closed loop that may e.g. have a length of 30 cm to 60 cm. The lanyard device 10 has a pendant 14 attached to the lanyard device. The pendant 14 is attached at a fixed position of the neck cord 12.

The lanyard device 10 includes a fiber optic Bragg grating strain sensor 30 having an optical fiber 32. A light source 34 in form of an infrared (IR) LED and a light detector 36 are coupled to the optical fiber 32. The optical fiber 32 includes multiple strain sensitive sections 38 which comprise Bragg gratings 40 responsive to respective IR wavelengths. The multiple strain sensitive sections 38 or Bragg gratings 40 are arranged one after another at different positions along the flexible neck cord 12 and form respective sensing elements of the sensor 30. The fiber optic Bragg grating strain sensor 30 is a reflection type fiber optic strain sensor. The light detector 36 is configured to selectively detect light reflected by the Bragg gratings 40 of the respective strain sensitive sections 38 for selectively sensing an amount of strain at the strain sensitive sections 38. The sensor 30 is configured for outputting a strain pattern comprising separate strain data respectively corresponding to sensed strain of the respective strain sensitive sections 38.

A power source 42, e.g. a battery, of the sensor 30 is accommodated in the pendant 14, as well as an electronic unit 50 for receiving the output of the sensor 30.

Figure 2:
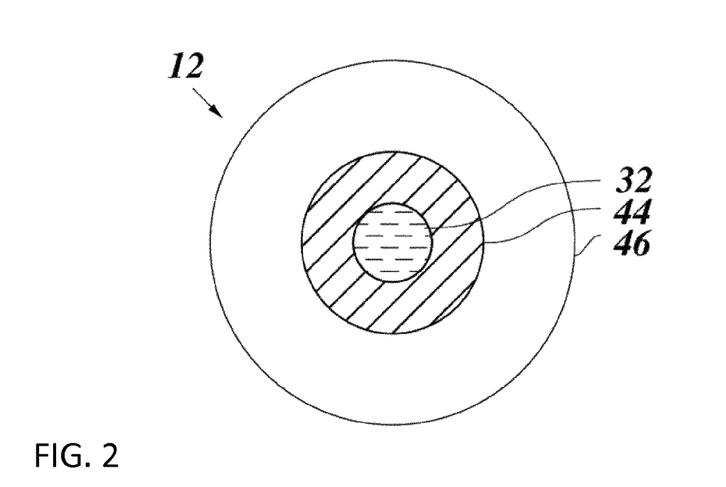
FIG. 2 schematically shows a cross-section of a neck cord.

FIG. 2 shows a cross-section of the neck cord 12. The neck cord 12 includes the optical fiber 32, a protective cladding 44 arranged around the optical fiber 32, and a soft textile cladding 46 woven around the fiber optic sensor wire 32, 44 for improving wearing convenience. The optical fiber 32 is fixedly attached to the pendant 14 or the cladding 44 or 46 at least at both ends of the extension of the optical fiber 32 over the strain sensitive sections 38 along the loop of the neck cord 12. This may improve the response of the strain sensor 30 to strain acting on the neck cord 12. For example, the optical fiber 32 may be directly attached to the pendant 14, to components inside the pendant 14, and/or attached to the pendant 14 through a mediating member, such as the cladding 44, 46.

Figure 3:
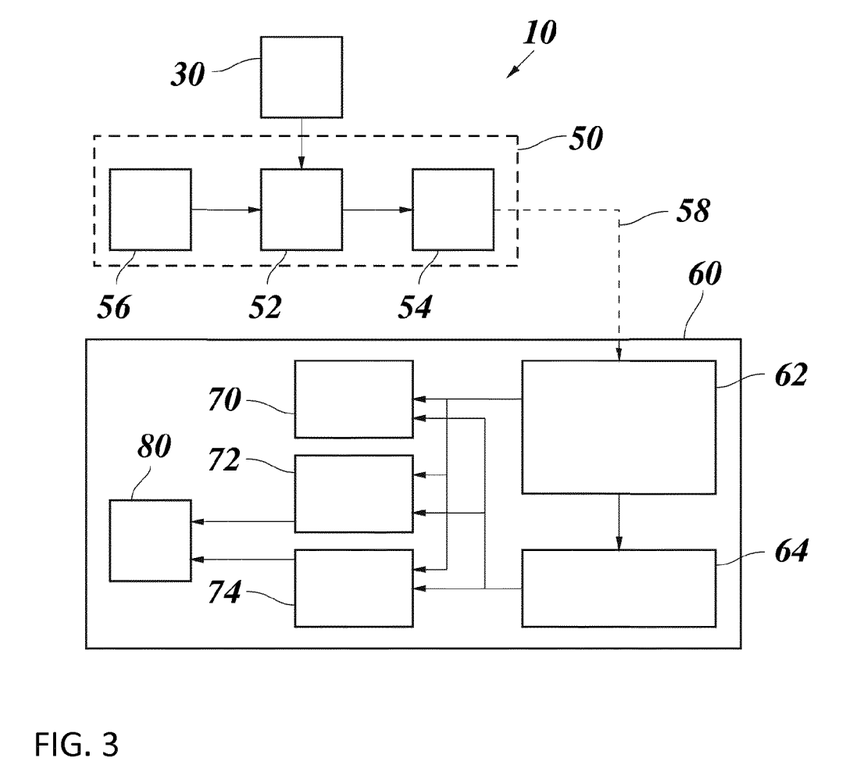
FIG. 3 shows a block diagram of the system of FIG. 1.

FIG. 3 shows a block diagram of the personal lanyard monitoring system. The electronic unit 50 of the pendant 14 includes a position recognition unit 52 and a wireless communication unit 54. The position recognition unit 52 receives strain data, in particular, strain patterns, from the strain sensor 30. By comparing a received strain pattern to pre-determined strain patterns pre-stored in a memory 56, the position recognition unit 52 recognizes a current position of the neck cord 12 that is associated with a selected one of the pre-determined strain patterns that closely resembles the current strain pattern.

Figure 4:
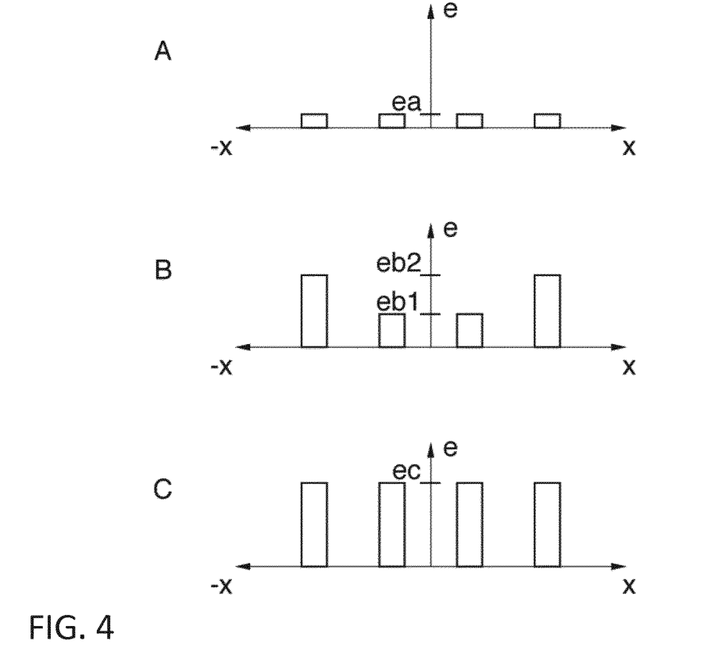
FIG. 4 schematically shows examples of strain patterns.

FIG. 4 shows examples A, B, C of pre-determined strain patterns. The patterns are for illustrative purposes. The graphs show strain e versus position x along the neck cord.

The strain pattern of example A is associated with a non-wearing position and has uniform, low strain values ea corresponding to the instrinsic strain of the neck cord, e.g. due to tensile strength in the cord material itself.

The strain pattern of example B is associated with a wearing position when worn around the neck of a person sitting or standing. It has medium strain values eb1 at positions that are assumed to at least partly rest on the neck, and high strain values eb2 at positions where the weight of the pendant 14 pulls on the neck cord in a straight line. in example B, friction or resistance of the garment and/or the body of a person wearing the lanyard device is assumed to reduce the effect of the pendant's weight.

The strain pattern of example C is associated with a non-wearing position and has uniform, high strain values ec corresponding to a neck cord suspended from a structure that has less width than a person's neck, such as a hook or a medium part of a coat hanger. For example, ec>eb2, since friction is assumed to be absent.

In general, strain patterns may be pre-determined for various positions and coded in the memory 56 in advance.

In FIG. 4, a position of x=0 corresponds to a position opposite to the pendant 14, which position may e.g. be assumed at the back side of the neck of a person wearing the lanyard device 10.

Returning to FIG. 3, position data 58 including the recognized position and a time stamp is transmitted by the wireless communication unit 52 to a receiving unit 62 of the communicator 60.

Over time, a series of strain patterns are derived from the respective current sensed strain of the strain sensitive sections 38 of sensor 30, together forming a spatial-temporal pattern of strain. The position recognition unit 52 thus outputs a time series of position data 56 (recognized positions and associated time stamp).

The communicator 60 includes a memory 64 for storing the received position data. Thus, over time, a series of position data may accumulate in the memory 64. For example, the memory 64 may be operated in a rolling manner for keeping the latest position data of a covered time span.

The communicator 60 includes an activity determining unit 70 which, based on the current and previous position data, determines a presumed activity of a person currently wearing the lanyard device 10.

For example, fluctuating positions or strain profiles of the lanyard device may be associated with physical activity like walking.

The communicator 60 further includes a fall detection unit 72 which, based on the current and previous position data, detects a fall of a person presumably wearing the lanyard device 10.

The communicator 60 further includes a non-wearing determining unit 74 which, based on the current and previous position data, determines a non-wearing state of the lanyard device 10.

For example, pre-determined strain profiles may be associated with different positions such as sitting, standing, walking, sleeping, falling, non-wearing etc. A relation between pre-determined strain profiles and actual positions of the lanyard device being worn by a specific user may e.g. be obtained from user trials in a calibration step.

The communicator 60 further includes a signaling unit 80 configured for sending an emergency signal or alert to a personal emergency response center, and for locally outputting a signal to a user.

The described position recognition, activity determining, and/or fall detection may further be based on output of further sensors, such as an accelerometer, a pressure sensor, a skin contact resistance sensor accommodated in the pendant 14 or the neck cord 12 of the lanyard device 10. For example, measured skin contact resistance may contribute to distinguish a non-wearing state from inactivity while wearing the lanyard device.

Figure 5:
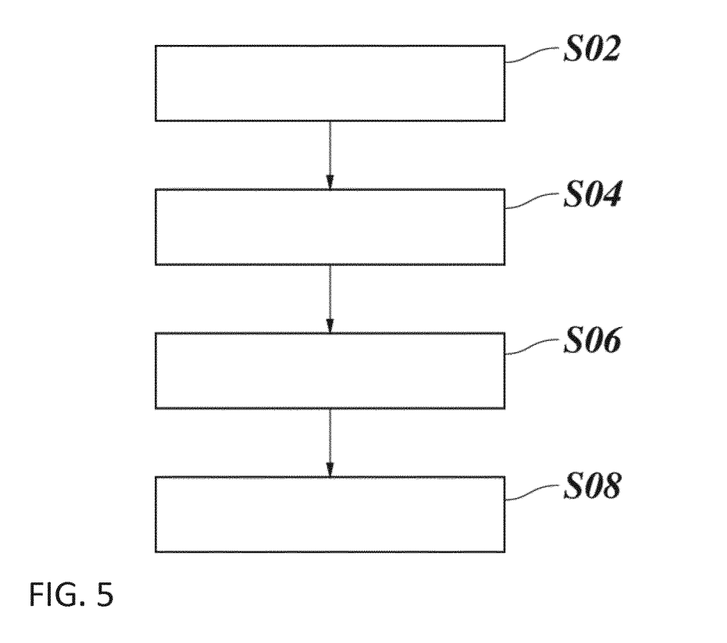
FIG. 5 schematically shows a method of initialization of a lanyard device system.

FIG. 5 shows steps of a method for personalizing a wearing strain pattern, which may be performed at the time of installing a personal lanyard device system. The method comprises step S02 of sensing strain at the sensing elements of sensor 30, step S04 of obtaining strain data from sensor 30, step S06 of initializing a personal wearing strain pattern based on the obtained strain data, and step S08 of storing the personal wearing strain pattern as a part of pre-determined strain data.

Figure 6:
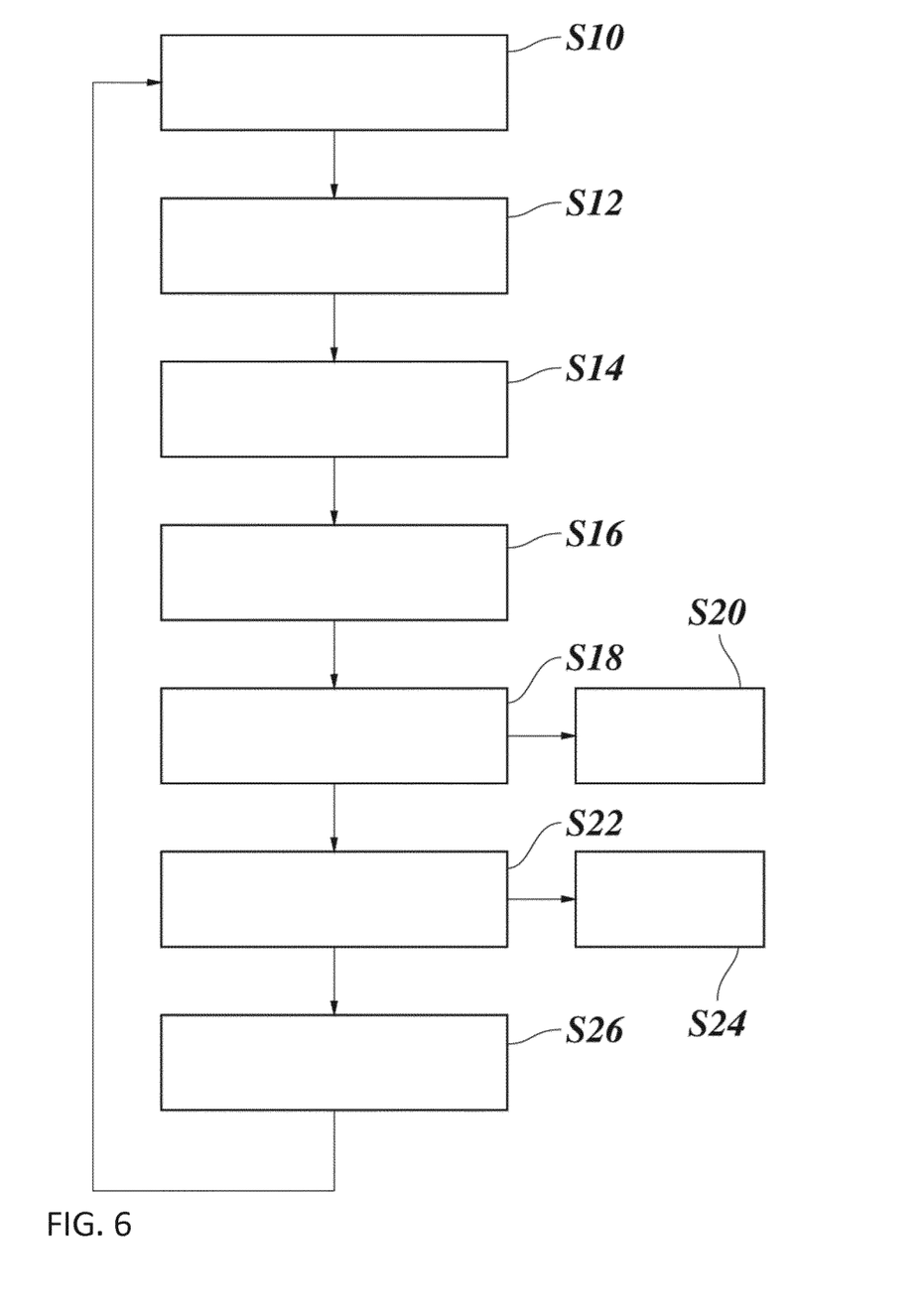
FIG. 6 schematically shows a method of monitoring a lanyard device of the system.

FIG. 6 shows steps of a method of monitoring the lanyard device 10, which may, for example, include the above personalizing method before step S10. The method comprises step S10 of sensing strain at the sensing elements of sensor 30, step S12 of obtaining strain data from sensor 30, and step S14 of comparing the obtained strain data to pre-determined strain data. Based on the result of the comparison, the position recognition unit 52 may perform step S16 of recognizing a position of the lanyard device, the fall detection unit 72 may perform step S18 of detecting a fall, the non-wearing determining unit 74 may perform step S22 of detecting a non-wearing state, and/or the activity determining unit 70 may perform step S26 of determining an activity. In case a fall is detected, step S20 of outputting an alert signal or message to the personal emergency response center is performed. In case a non-wearing state is determined, this is signalized by the communicator locally and/or to the personal emergency response center.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A personal lanyard monitoring system comprising:
a lanyard device comprising:
a flexible neck cord comprising at least two sensing elements arranged one after another at different positions along the flexible neck cord;
at least one strain sensor arranged for sensing strain in the flexible neck cord, wherein the at least one strain sensor is configured to output separate strain data respectively corresponding to sensed strain of the at least two respective sensing elements; and
a communication unit for wirelessly transmitting data derived from the sensed strain; and
a communicator remote from the lanyard device, wherein the communicator comprises a receiving unit for wirelessly receiving data from the communication unit of the lanyard device,
wherein at least one of the lanyard device and the communicator comprises a position recognition unit configured to:
compare the strain data output from the at least one strain sensor to pre-determined strain data; and
recognize a position of the flexible neck cord in dependence on a result of the comparison.

2. The lanyard device of claim 1, wherein the at least one strain sensor comprises at least one fiber optic strain sensor.

3. The lanyard device of claim 2, wherein:
the at least one fiber optic strain sensor comprises an optical fiber which comprises at least two strain sensitive sections forming the at least two sensing elements of the at least one fiber optic strain sensor, the at least two strain sensitive sections being arranged one after another at different positions along the flexible neck cord; and
the at least one fiber optic strain sensor is configured to output the separate strain data respectively corresponding to the sensed strain of the at least two respective sensing elements formed by the at least to respective strain sensitive sections.

4. The lanyard device of claim 1, further comprising a pendant attached to the flexible neck cord, the pendant comprising a power source of the at least one strain sensor.

5. The personal lanyard monitoring system of claim 1, wherein at least one of the lanyard device and the communicator comprises an activity determining unit configured to determine an activity in dependence on a result of a comparison of the strain data output from the at least one strain sensor to pre-determined strain data.

6. The personal lanyard monitoring system of claim 1, wherein at least one of the lanyard device and the communicator comprises a fall detection unit configured to detect a fall of a person presumably wearing the lanyard device in dependence on a result of a comparison of the strain data output from the at least one strain sensor to pre-determined strain data.

7. The personal lanyard monitoring system of claim 1, wherein at least one of the lanyard device and the communicator comprises a non-wearing determining unit configured to determine a non-wearing state of the lanyard device in dependence on a result of a comparison of the strain data output from the at least one strain sensor to predetermined strain data associated with non-wearing of the lanyard device.

8. A personal lanyard monitoring system comprising:
a lanyard device comprising:
a flexible neck cord;
at least one strain sensor arranged for sensing strain in the flexible neck cord; and
a communication unit for wirelessly transmitting data derived from the sensed strain; and
a communicator remote from the lanyard device, wherein the communicator comprises a receiving unit for wirelessly receiving data from the communication unit of the lanyard device,
wherein at least one of the lanyard device and the communicator comprises a position recognition unit configured to:

compare the strain data output from the at least one strain sensor to pre-determined strain data, wherein the strain data and the pre-determined strain data both comprise at least one respective spatial and/or temporal pattern of strain; and recognize a position of the flexible neck cord in dependence on a result of the comparison.

9. The personal lanyard monitoring system of claim 1, wherein at least one of the lanyard device and the communicator is configured to:

initialize at least one personal wearing strain pattern based on the strain data output from the at least one strain sensor; and store the at least one personal wearing strain pattern as a part of pre-determined strain data.

10. A method of recognizing a position of a flexible neck cord of a lanyard device, the method comprising:

sensing strain in the flexible neck cord, the flexible neck cord comprising at least two sensing elements arranged one after another at different positions along the flexible neck cord;

obtaining separate strain data respectively corresponding to the sensed strain of the at least two respective sensing elements;

comparing the obtained strain data to pre-determined strain data; and recognizing a position of the flexible neck cord in dependence on a result of the comparison.

11. The method according to claim 10, further comprising at least one of:

determining an activity in dependence on the result of the comparison;

detecting a fall of a person presumably wearing the lanyard device in dependence on the result of the comparison; and determining a non-wearing state of the lanyard device in dependence on the result of the comparison.

\* \* \* \* \*